(12) United States Patent
Houde

(10) Patent No.: US 6,834,842 B2
(45) Date of Patent: Dec. 28, 2004

(54) FLUID MANAGEMENT VALVE

(75) Inventor: Eric Houde, Saratoga Springs, NY (US)

(73) Assignee: SciMed Life Systems, Inc., Maple Grove, MN (US)

( * ) Notice: Subject to any disclaimer, the term of this patent is extended or adjusted under 35 U.S.C. 154(b) by 330 days.

(21) Appl. No.: 10/043,052

(22) Filed: Jan. 9, 2002

(65) Prior Publication Data

US 2003/0127620 A1 Jul. 10, 2003

(51) Int. Cl.[7] ................................................ F16K 7/06
(52) U.S. Cl. ..................... 251/7; 251/149.1; 251/251; 604/167.01; 604/905
(58) Field of Search .................. 251/4, 7, 8, 149.1, 251/149.4, 229, 251, 262; 604/167.01, 256, 167.03, 905, 167.06; 285/390, 394

(56) References Cited

U.S. PATENT DOCUMENTS

| | | | | |
|---|---|---|---|---|
| 278,008 | A | * | 5/1883 | Haley .......................... 251/251 |
| 3,920,215 | A | * | 11/1975 | Knauf ............................ 251/7 |
| 4,243,034 | A | * | 1/1981 | Brandt .................. 604/167.01 |
| 4,378,013 | A | * | 3/1983 | LeFevre ........................ 251/7 |
| 4,886,507 | A | | 12/1989 | Patton et al. |
| 5,009,391 | A | | 4/1991 | Steigerwald |
| 5,080,654 | A | * | 1/1992 | Picha et al. ............ 604/167.02 |
| 5,127,626 | A | * | 7/1992 | Hilal et al. .............. 251/149.1 |
| 5,167,636 | A | | 12/1992 | Clement |
| 5,282,790 | A | | 2/1994 | Clement |
| 5,356,375 | A | | 10/1994 | Higley |
| 5,378,229 | A | | 1/1995 | Layer et al. |
| 5,423,751 | A | | 6/1995 | Harrison et al. |
| 5,490,536 | A | * | 2/1996 | Cole et al. .................. 251/251 |
| 5,533,978 | A | | 7/1996 | Terstein |
| 5,569,208 | A | | 10/1996 | Woelpper et al. |
| 5,573,515 | A | | 11/1996 | Wilson et al. |
| 5,618,268 | A | | 4/1997 | Raines et al. |
| 5,693,025 | A | | 12/1997 | Stevens |
| 5,800,397 | A | | 9/1998 | Wilson et al. |
| D404,717 | S | | 1/1999 | Duchon et al. |
| 5,916,165 | A | | 6/1999 | Duchon et al. |
| 5,935,112 | A | | 8/1999 | Stevens et al. |
| 5,988,587 | A | | 11/1999 | Duchon et al. |
| 6,030,368 | A | | 2/2000 | Anwar et al. |
| 6,325,092 | B1 | * | 12/2001 | Pirkle ...................... 251/149.6 |
| 6,402,723 | B1 | * | 6/2002 | Lampropoulos et al. .... 604/256 |

FOREIGN PATENT DOCUMENTS

| | | |
|---|---|---|
| WO | WO 99/24094 | 5/1999 |
| WO | WO 00/53242 | 9/2000 |
| WO | WO 00/62844 | 10/2000 |

OTHER PUBLICATIONS

International Search Report; PCT/US02/41812 dated May 15, 2003.

* cited by examiner

Primary Examiner—Eric Keasel
(74) Attorney, Agent, or Firm—Marshall, Gerstein & Borun LLP

(57) ABSTRACT

A fluid management system is disclosed which includes an injection device, a medical device, and a valve. The medical device is in fluid communication with the injection device. The valve is operatively associated with the medical device, and the valve includes a mechanism for slidably opening the valve.

14 Claims, 4 Drawing Sheets

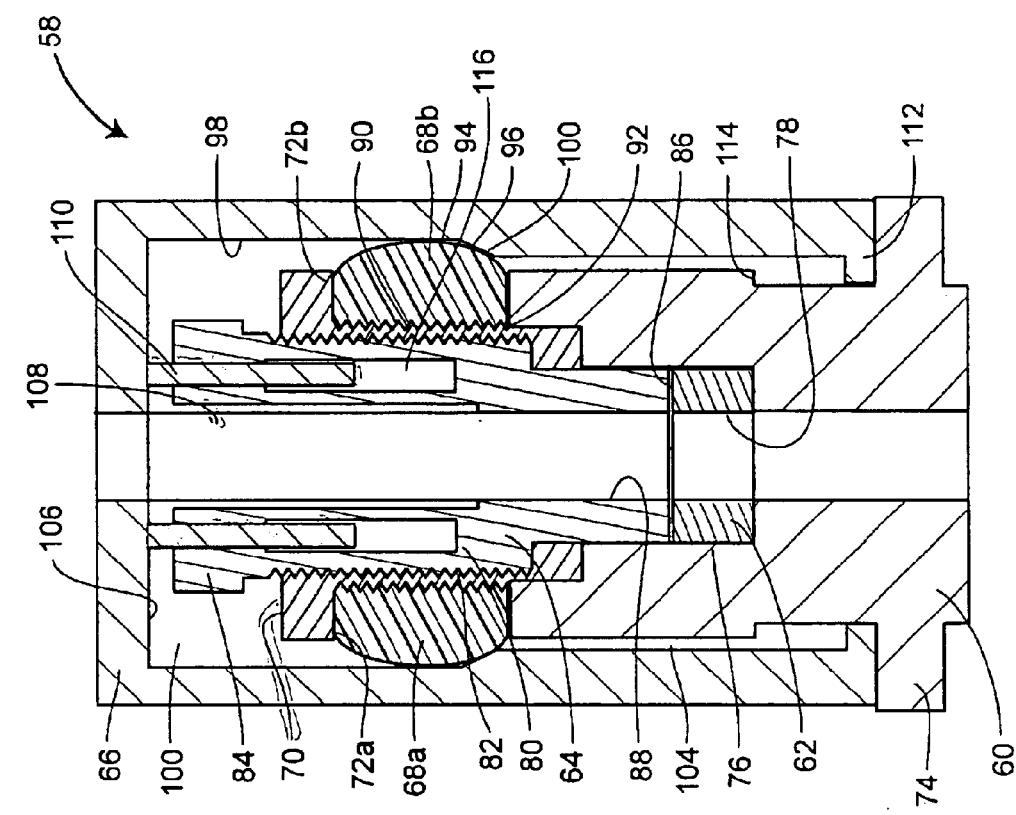
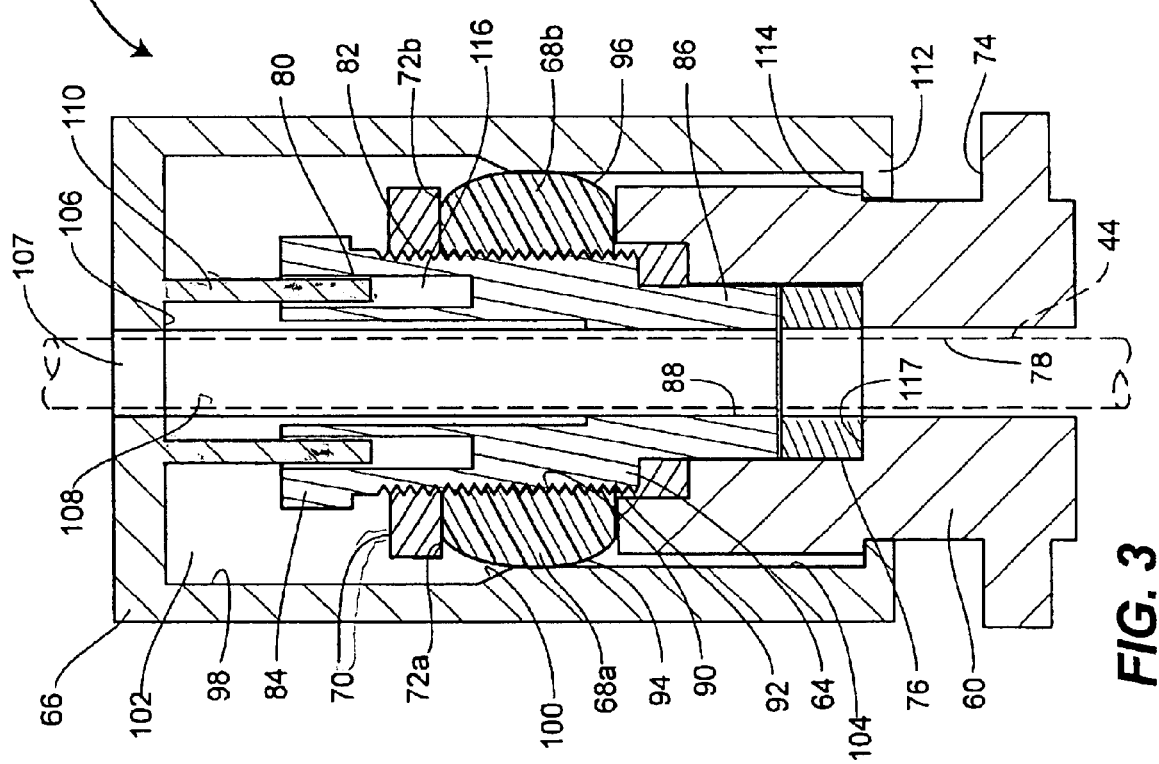

FLUID MANAGEMENT VALVE

FIELD OF THE INVENTION

The invention generally relates to medical devices and, more particularly, relates to devices for controlling fluid flow in an injection system.

BACKGROUND OF THE INVENTION

It is often necessary to open and close conduits in medical procedures. For example, in an angiographic procedure, at least one syringe is provided which draws from a supply of radiopaque contrast and injects the contrast through a catheter into the patient. The catheter may be connected directly to the syringe, or other equipment may be provided therebetween, such as a manifold or a y-adaptor. The y-adaptor may be provided to receive fluid from one or more sources to the same catheter or may be provided to provide one inlet for a manifold, and a second inlet for interventional devices.

Currently, y-adaptors include hemostatic valves to minimize blood loss from the patient. The hemostatic valve includes a cylindrical gland that is compressed by a collar to change the diameter of the gland. By inserting a catheter through the gland and then changing the diameter of the gland, the gland compresses the catheter sufficiently to provide hemostatis and fix the catheter into location. The compression of the gland by the collar is typically achieved by twisting a cap on the y-adaptor. The y-adaptor includes threads mated with threads provided on a body of the y-adaptor. As the cap is twisted onto the body, a cap moves toward the y-adaptor body and the collar is compressed.

Often, the cap must be turned several times, depending on the amount of compression required to achieve the desired seal. For example, during typical cardiology procedures using such y-adaptors, there are numerous times that physicians need to open or close the gland for intervention, removal and manipulation of each interventional device. Occasionally the y-adaptor is used to fix a catheter shaft into position. It is not uncommon for physicians to require more than one adjustment of the catheter.

Conventionally, passive valves (normally closed valves) are provided which can be forced open when adequate force is imparted against the valve element by the device being inserted. Currently, such passive devices may require relatively more force to be opened.

SUMMARY OF THE INVENTION

In accordance with one aspect of the invention, a fluid management system is provided which comprises an injection device, a medical device, and a valve. The medical device is in fluid communication with the injection device. The valve is operatively associated with the medical device and the valve includes a mechanism for slidably opening the valve.

These and other aspects and features of the invention will become more apparent from the following detailed description when taken in conjunction with the accompanying drawings.

BRIEF DESCRIPTION OF THE DRAWINGS

FIG. 3 is a sectional view of the valve of FIG. 2 and depicted in a locked position;

FIG. 4 is a sectional view of the valve of FIG. 2 and depicted in a released position;

Figure 1:
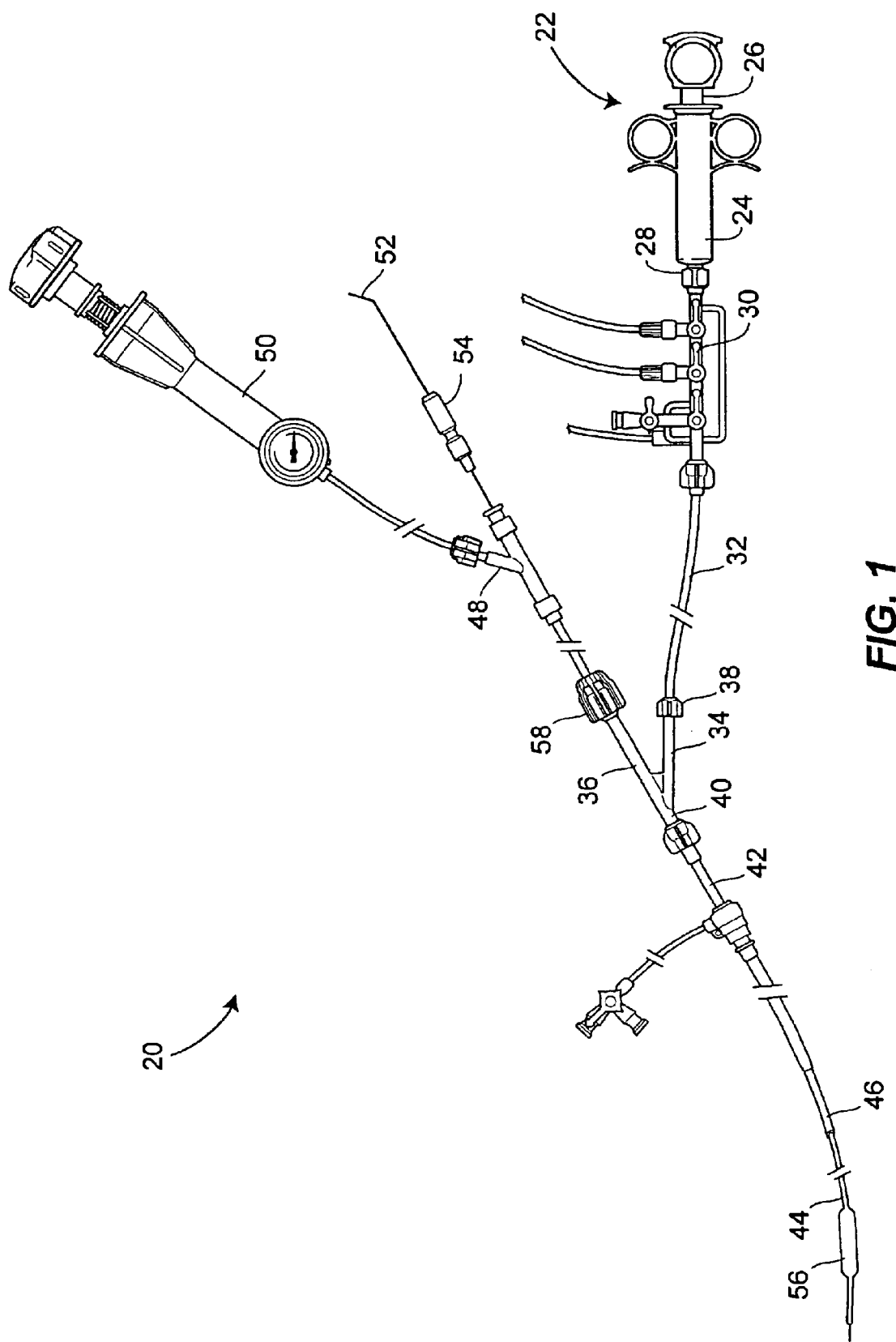
FIG. 1 is a side view of an injection system constructed in accordance with the teachings of the invention.

While the invention is susceptible to various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions, and equivalents falling within the spirit and scope of the invention as defined by the appended claims.

DETAILED DESCRIPTION OF THE PREFERRED EMBODIMENTS

Referring now to the drawings, and with specific reference to FIG. 1, an interventional system constructed in accordance with the teachings of the invention is generally depicted by reference numeral 20. While the teachings of the invention will be described in conjunction with such an interventional system 20, it is to be understood that the teachings of the invention can be employed in multiple other applications, wherever conduits need to be quickly and securely opened and closed.

As shown in FIG. 1, the system 20 includes an injection device 22. The injection device 22 may be a manually operated syringe, but could be alternatively provided as by a power injection system as well. The depicted syringe 22 includes a cylinder 24 in which an operable plunger 26 is disposed for reciprocating motion. The syringe 22 includes an outlet 28 to which a manifold 30 is connected. The manifold 30 may be connected to multiple fluid supplies, such as, but not limited to, radiopaque contrast for use in conjunction with angiographic procedures.

A fluid supply line 32 extends from the manifold 30 and is connected to a y-adaptor 34. The y-adaptor 34 includes first and second inlets 36, 38 and a single outlet 40. A guide catheter 42 is connected to the outlet 40, with a balloon catheter 44 within the lumen of the guide catheter 42 and extending from the introducer sheath 46 connected to the guide catheter 42 and through the first inlet 36 of the y-adaptor 34. Upstream of the first inlet 36 is a balloon inflation port 48 on the balloon catheter 44 to which an inflation device 50 is connected. A guide wire 52 and torque device 54 also enter proximate the inflation port 48 for control of the balloon 56 of the balloon catheter 44.

As can be seen from FIG. 1, a hemostatic valve 58 is positioned at the first inlet 36. The valve 58 is able to open and close around a medical device, such as the balloon catheter 44, extending therethrough in either a fast or slow fashion. For example, it may be advantageous to quickly open the valve 58 as when exchanging catheters or introducing stents or balloons. It would also be advantageous to provide a mechanism through which the valve 58 can be securely closed with an effective seal. It is to be understood that the medical device could be items other than catheters, such as guide wires and the like as well.

Figure 2:
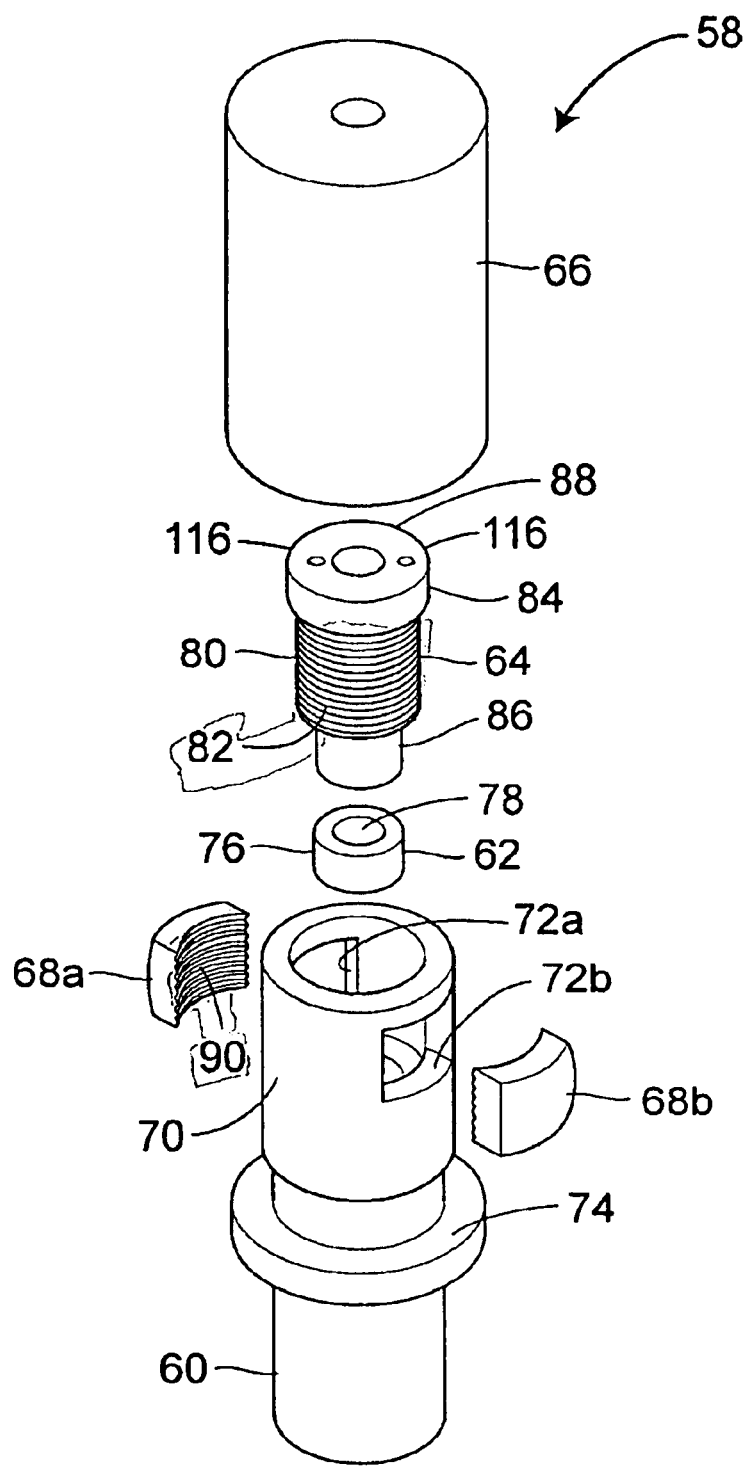
FIG. 2 is an exploded view of a valve constructed in accordance with the teachings of the invention.

Turning now to FIGS. 2–4, the valve 58 is shown in further detail. The valve 58, in one embodiment includes a body 60, a gland 62, a collar 64, a cap 66, and first and second half nuts 68a and 68b. The body 60 includes a cylindrical head 70 in which first and second arcuate apertures 72a and 72b are provided. The body further includes an annular flange 74, the importance of which will be further described herein. If more or less than two half nuts 68 are provided, a corresponding number of apertures 72 may be provided within the cylindrical head 70 of the body 60.

The gland 62 is preferably manufactured from an elastomeric material and includes a substantially cylindrical outer surface 76 as well as a central bore 78.

The collar 64 includes a central portion 80 provided with external threads 82 (FIGS. 3 and 4). The collar 64 further includes an enlarged diameter platform 84 and a driving end 86. A central bore 88 extends through the collar 64.

The first and second half nuts 68a and 68b include threads 90 (FIGS. 3 and 4) on an internal surface 92 thereof, as well as cam surfaces 94 provided on an external surface 96 thereof.

The cap 66 includes an interior surface 98 having a cam surface 100 positioned between an enlarged diameter area 102 and a reduced diameter area 104. The cap 66 further includes a top surface 106 having an inlet 107 from which a tube 108 downwardly extends, as well as at least one drive shaft 110. A radially inwardly directed lip 112 is provided at the base of the cap 66 and is adapted to slide on the body 60 between a shoulder 114, and the annular flange 74.

In alternative embodiments, the locations of the threads and cam surfaces may be different. For example, the interior surface 98 of the cap 66 may include threads (not shown) for engagement with threads on the exterior surface 96 of the nuts 68a and 68b. In such an embodiment, cam surfaces could be provided on the internal surface 92 of the nuts 68a, 68b for cooperation with cam surfaces on the central portion 80 of the collar 64. In so doing, the cap 66 may be rotated or slid relative to the remainder of the valve 58 for operation of the valve 58 in a secure close mode or a quick release mode, respectively.

In operation, if the valve 58 is positioned with the cap 66 in the position of FIGS. 2 and 3, the half nuts 68a and 68b are driven radially inwardly by the cam surface 100 of the cap 66. Accordingly, the threads 90 and 82 are engaged. Since the drive shaft 110 is rotationally fixed to the collar 64 through a channel 116, rotation of the cap 66 causes the collar 64 to rotate as well. Since the first and second half nuts 68a and 68b are axially fixed by the body 60, rotation of the cap 66 in a first direction causes the collar 64 to axially advance in a first direction, with rotation of the cap 66 in the opposite direction causing the collar 64 to axially translate in the opposite direction.

When the collar 64 axially advances toward the gland 62, the gland 62 is pushed against a land 117 of the body 60 and compresses, thereby exerting inward force on the catheter 44 provided through the valve 58. If the collar 64 is advanced sufficiently, the gland 62 compresses sufficiently to complete the seal of the catheter 44.

Since rotation of the cap 66 can be relatively time consuming, the valve 58 is further provided with a quick release feature. As can be seen from a comparison of FIGS. 2 and 3, if the cap 66 is axially slid toward the body 60, the threads 82 and 90 become disengaged. Accordingly, the gland 62 is no longer compressed and can return to its normal position, opening the catheter 44. The force of the expanding gland 62 pushes against the driving end 86 of the collar 64 to thereby push the collar 64 upward, and the first and second half nuts 68a and 68b radially outward, to the point of disengagement. In an alternative embodiment, a spring may be provided to assist the expansion motion by the gland 62.

Figure 7:
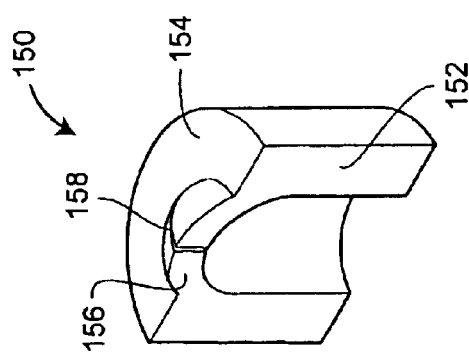
FIG. 7 is an isometric cut-away view of a slitted gland constructed in accordance with the teachings of the invention.
Figure 6:
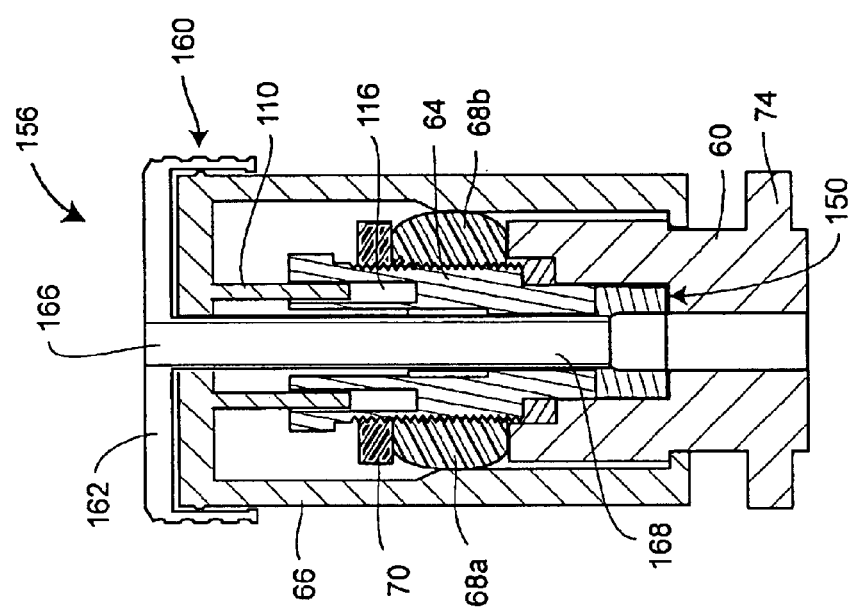
FIG. 6 is a sectional view of the alternate embodiment of FIG. 5, but depicted in an open position.
Figure 5:
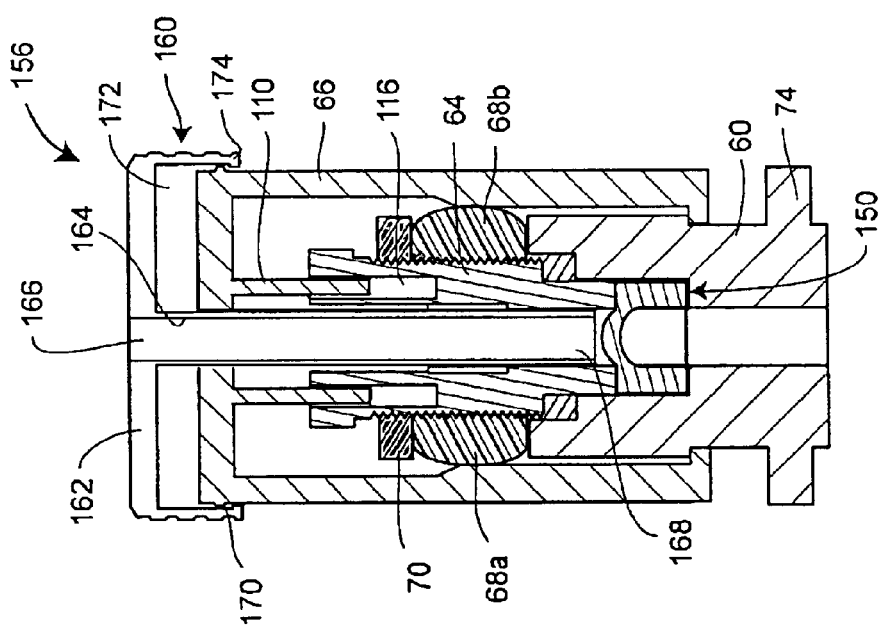
FIG. 5 is a sectional view of an alternative embodiment of the invention and depicted in a closed position.

Referring now to FIGS. 5–7, an alternative embodiment of a valve is generally referred to by reference numeral 156. Wherein like elements are employed in the alternative embodiment, like reference numerals are employed. A difference in the alternative embodiment is with regard to the gland 150. As shown best in FIG. 7, the gland 150 includes a cylindrical base 152 having a top 154 across which a web 156 extends. A linear slit 158 is provided within the web 156. The web 156 is preferably concave or bulbous and extends away from the cylindrical base 152.

Another difference in the alternative embodiment is illustrated in FIGS. 5 and 6 wherein the valve 58 is shown to include a shuttle 160. The shuttle includes an upper cap 162 from which an actuation conduit 164 downwardly extends. The actuation conduit 164 includes an inlet 166 and an outlet 168. As can be seen in the comparison between FIGS. 5 and 6, the shuttle 160 can be moved between open and closed positions. In the open position, the shuttle 160 is downwardly depressed into the valve 58 thereby forcing the outlet 168 through the slit 158 of the gland 150. In so doing, the gland 150 is held open with the web 156 surrounding the actuation conduit 164. Accordingly, a pathway is created from the inlet 166, through the actuation conduit 164, and through the central bore 78 of the body 60. In such an orientation, a device, such as a stent (not shown) or the balloon 56 may be easily inserted through the valve 58 without interference from the gland 150.

Conversely, when the shuttle 160 is pulled away from the valve 58, the actuation conduit 164 is pulled away from the gland 150 and the resiliency of the elastomeric gland 150 causes the web 156 to return to a closed position wherein the slit 158 is sealingly closed. A circumferential nib 170 may be provided on the cap 66. In combination with a shoulder 172 and a radially inwardly directed lip 174 provided on the shuttle 160, the circumferential nib 170 prevents the shuttle 160 from being fully retracted off of the valve 58.

In operation, it can therefore be seen that the teachings of the invention can be used to construct the a fluid management system having a valve operable in secure close and quick release modes. This not only minimizes blood loss and accurate positioning of catheters, but allows for quick interchange of catheters as well.

What is claimed is:

1. A valve, comprising:
   a body having an outer surface, an inlet, and an outlet;
   at least one nut movably mounted within the body outer surface, the nut having internal threads and an external cam surface;
   a collar mounted within the body inlet and including external threads adapted to mate with the internal threads of the nut;
   an elastomeric gland between the body outlet and the collar; and
   a cap having a drive shaft and a cam surface, the cap being movable between locked and released positions, the cam surface positioning the nut threads into engagement with the collar threads when the cap is in the locked position, the gland positioning the nut threads out of engagement with the collar threads when the cap is in the released position.

2. The valve of claim 1, wherein the body outer surface includes first and second apertures and wherein the valve includes first and second nuts movably mounted in the first and second apertures, respectively.

3. The valve of claim 1, wherein the cap is rotationally fixed to, and axial movable relative to, the collar.

4. The valve of claim 3, wherein the drive shaft is axially slidable within a channel provided within the collar.

5. The valve of claim 1, wherein the cap includes an outlet adapted to receive a catheter.

6. The valve of claim 1, wherein the body includes an inlet adapted to receive a catheter.

7. The valve of claim 1, wherein the cap includes an inwardly directed lip adapted to slide between a flange and a shoulder provided in spaced relation on the body.

8. The valve of claim 1, wherein the gland is an elastomeric cylinder.

9. The valve of claim 1, wherein the gland includes a passive valve element.

10. The valve of claim 9, wherein the passive valve element is a web of elastomeric material extending across the gland, the web including a slit therethrough.

11. The valve of claim 1, further including a shuttle element adapted to move between open and closed positions, the shuttle element holding the passive valve element open when in the open position, the passive valve element being normally in the closed position.

12. The valve of claim 11, wherein the shuttle includes a central conduit adapted to hold the passive valve element open when the shuttle is depressed into the cap.

13. The valve of claim 1, wherein the valve is operable in a quick open mode and a secure close mode.

14. The valve of claim 1, wherein the gland includes a slitted web.

* * * * *